(12) United States Patent
Sambasivam

(10) Patent No.: US 7,858,836 B2
(45) Date of Patent: Dec. 28, 2010

(54) ENZYME INHIBITING ADHESIVES

(75) Inventor: Mahesh Sambasivam, Pennington, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 258 days.

(21) Appl. No.: 11/288,610

(22) Filed: Nov. 29, 2005

(65) Prior Publication Data

US 2006/0141016 A1 Jun. 29, 2006

Related U.S. Application Data

(60) Provisional application No. 60/639,381, filed on Dec. 27, 2004.

(51) Int. Cl.
*A61F 13/00* (2006.01)
*C08L 3/02* (2006.01)

(52) U.S. Cl. .................. 602/48; 523/111; 523/118

(58) Field of Classification Search ......... 604/330–344; 524/505
See application file for complete search history.

(56) References Cited

U.S. PATENT DOCUMENTS

| | | | |
|---|---|---|---|
| 5,496,296 A * | 3/1996 | Holmberg | 604/336 |
| 5,730,736 A * | 3/1998 | Sawers et al. | 604/344 |
| 6,207,596 B1 | 3/2001 | Rourke et al. | |
| 6,331,295 B1 | 12/2001 | Schulz | |
| 6,558,792 B1 * | 5/2003 | Vaabengaard et al. | 428/355 CP |
| 6,599,523 B2 * | 7/2003 | Cohen et al. | 424/443 |
| 6,723,354 B1 * | 4/2004 | Ruseler-van Embden et al. | 424/725 |
| 6,746,765 B1 | 6/2004 | Fattman | |
| 2002/0128345 A1 | 9/2002 | Paul | |
| 2003/0104019 A1 | 6/2003 | McCulloch et al. | |
| 2003/0206944 A1 | 11/2003 | Cohen et al. | |
| 2004/0028708 A1 | 2/2004 | Brooks | |
| 2004/0065232 A1 * | 4/2004 | Lykke | 106/680 |
| 2004/0166183 A1 | 8/2004 | Ruseler-van Embden et al. | |
| 2007/0051376 A1 * | 3/2007 | Kulichikhin et al. | 128/894 |

OTHER PUBLICATIONS

Rusler-van Embden et al., Potato tuber proteins efficiently inhibit faecal proteolytic activity: implications for treatment of peri-anal dermatis, Apr. 2004, European Journal of Clinical Investigation, 34(4):303-311.*

* cited by examiner

*Primary Examiner*—Kim M Lewis
(74) *Attorney, Agent, or Firm*—Stuart E. Krieger

(57) ABSTRACT

An adhesive composition including an adhesive component and an enzyme inhibiting component for use in ostomy and wound care applications. The enzyme inhibitors are derived from tubers, such as potatoes. In ostomy, the adhesive composition helps to secure the collection bag or pouch to the skin. In wound care application, the adhesive composition secures the wound dressing to the skin. The adhesive composition also may be used to couple two or more ostomy or wound care components together.

4 Claims, 4 Drawing Sheets

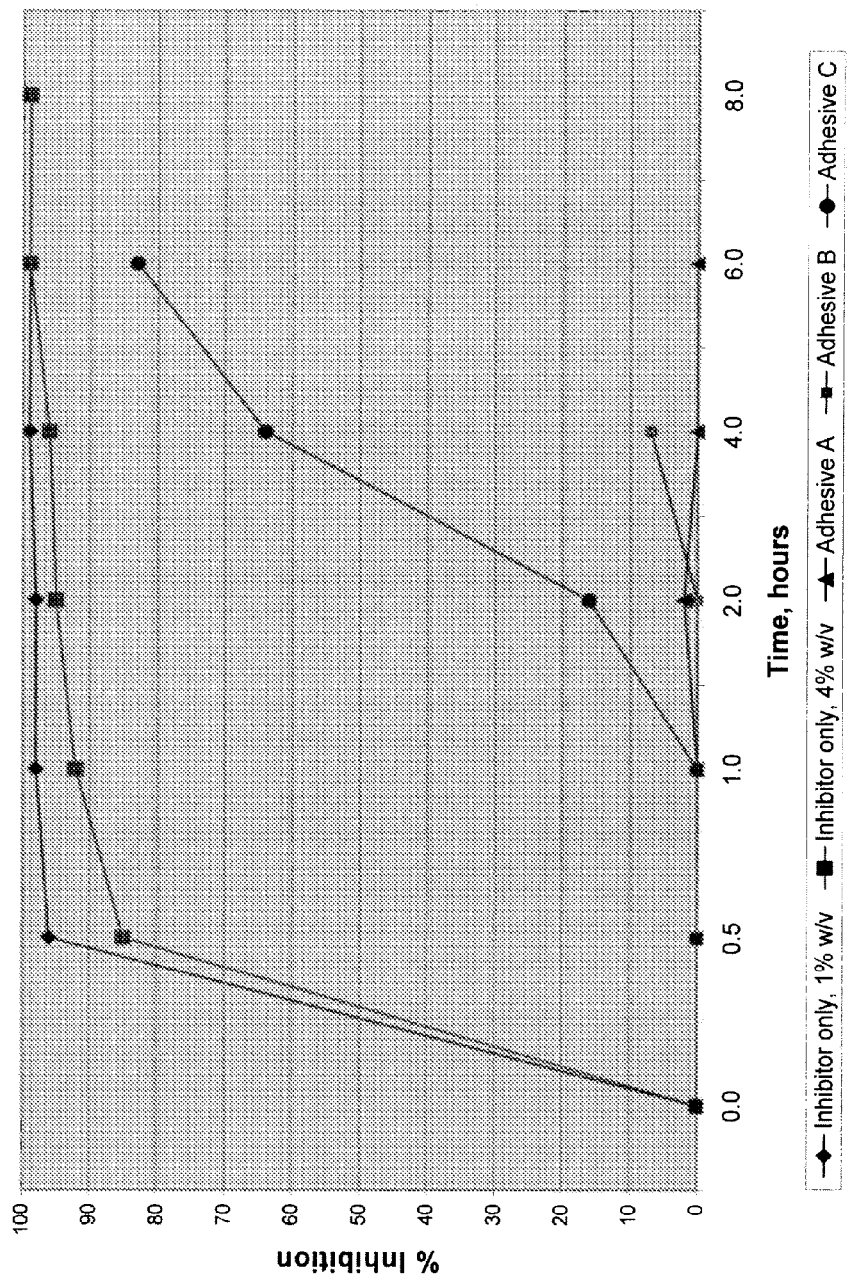

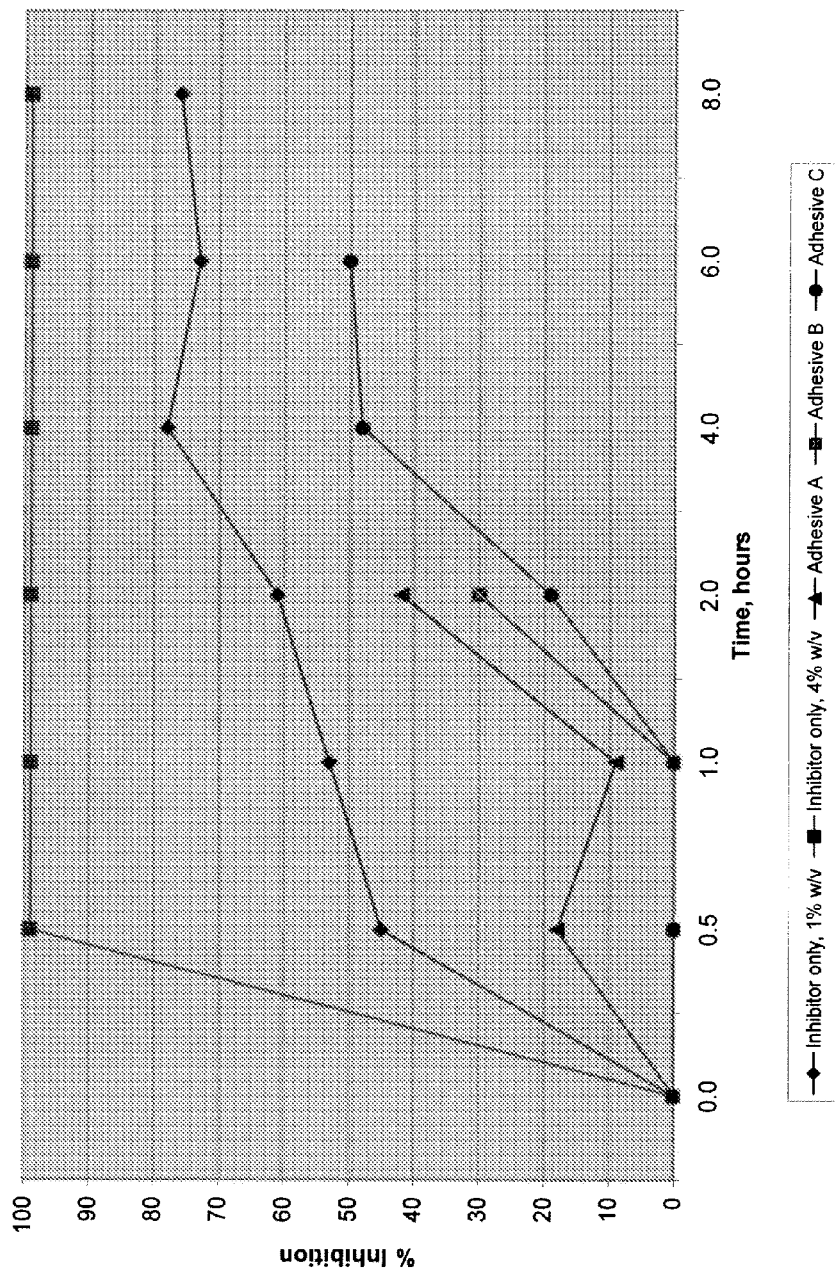

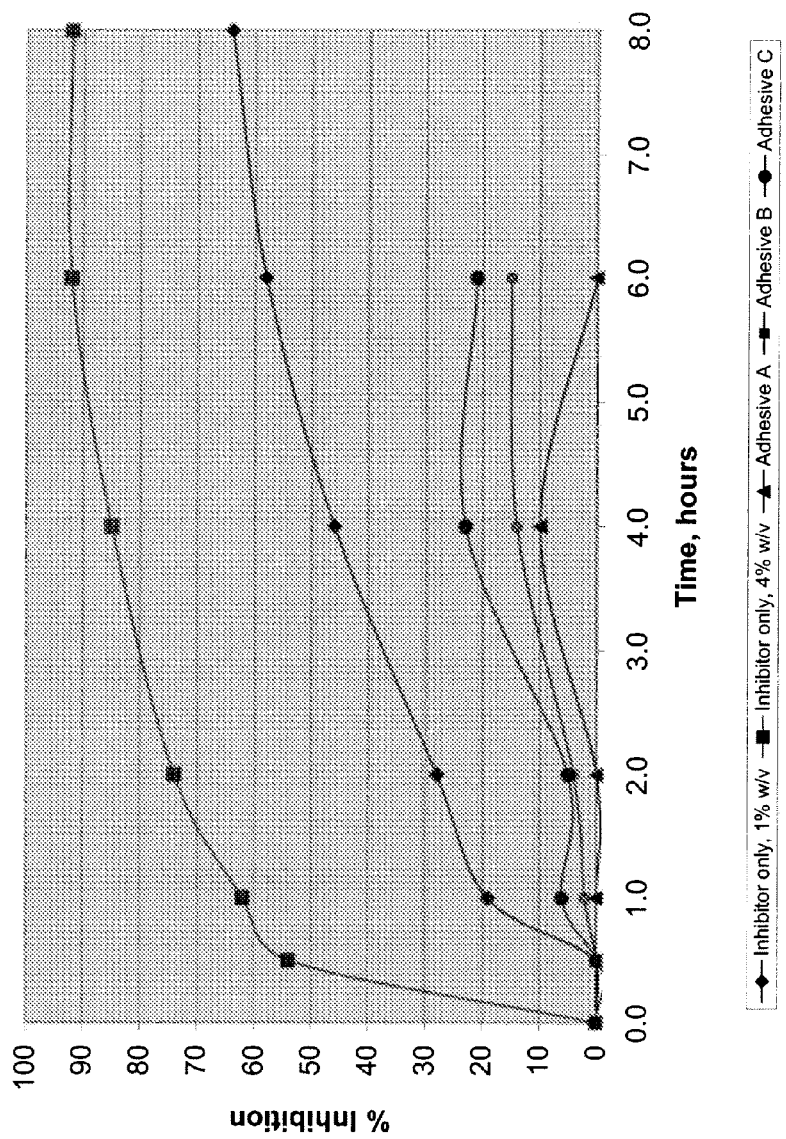

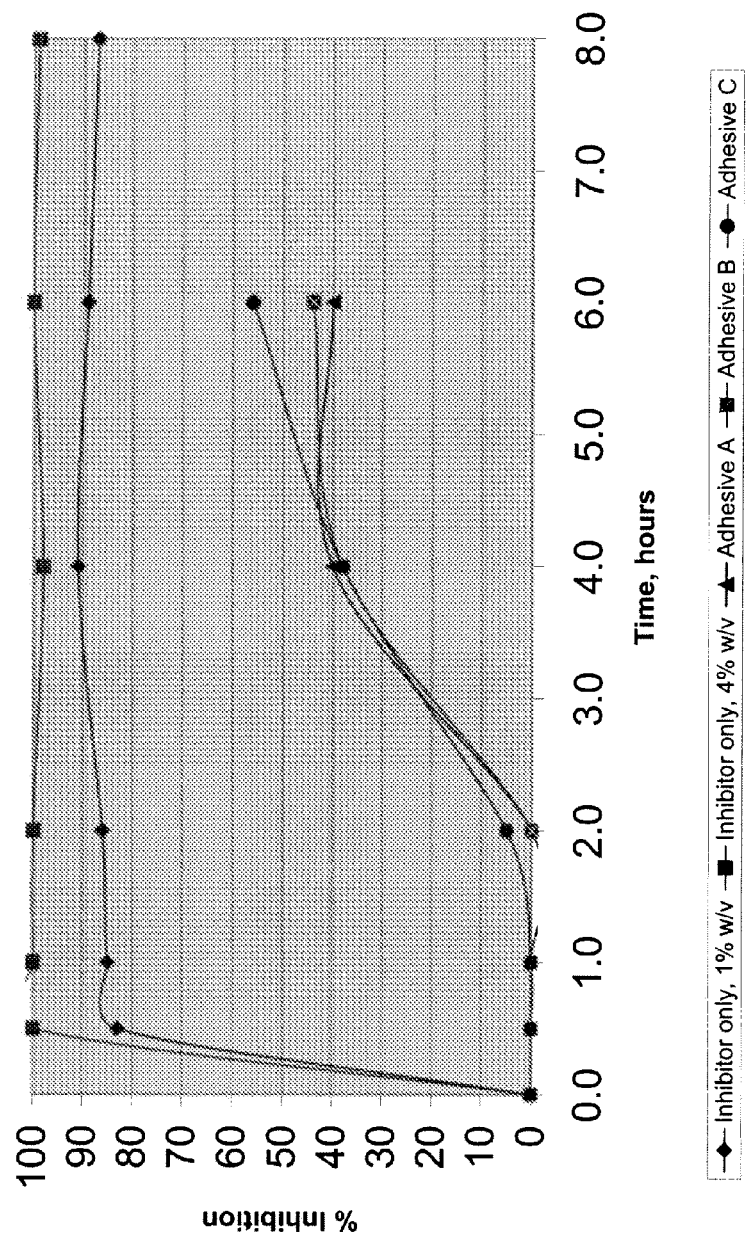

ENZYME INHIBITING ADHESIVES

This application claims the benefit of U.S. Provisional Application No. 60/639,381, filed 27 Dec. 2004 and is hereby incorporated by reference in their entirety.

FIELD OF INVENTION

This invention relates to an adhesive for use in an ostomy or wound care device, in particular, an adhesive which contains enzyme inhibitors.

BACKGROUND OF INVENTION

The peristomal, perianal, and perineal skin in subjects with an ostomy or fecal incontinence, and infants wearing diapers can be continuously exposed to feces. When this occurs, the skin is attacked by the contents of feces, mainly the proteolytic or digestive enzymes. This leads to erosion of the skin surface resulting in severe skin conditions, such as dermatitis. Similar skin erosion could also occur in peri-wound skin in a wound environment.

In the case of ostomates, a variety of products are used in an attempt to protect the skin from fecal or urine contact. These include adhesive wafers, lotions, creams, pastes, rings, barrier wipes, etc. However, all of these methods of protection only offer a physical barrier to enzymatic attack. When the physical barrier wears out or breaks, the enzymatic attack is imminent. In the case of ostomates, another drawback is that pre-treatments to the skin, such as lotions or creams, may negatively affect the adhesion of the adhesive wafer to the skin. This can lead to premature failure by detachment of the ostomy device, which is not acceptable.

In the case of a wound, enzymes such as elastase potentially cause skin damage and retard wound healing.

The present invention is related to the protection of the skin using an adhesive composition which contains enzyme inhibiting additives while maintaining the function of the adhesive and the inhibitors.

PRIOR ART

There are numerous prior art disclosures that describe the use of enzyme inhibitors in lotions and pastes, powders, etc.

U.S. Pat. No. 6,723,354 and Patent Application US 2004/0166183A1 disclose the use of potato juice in the form of sprays, gel, lotions, powder, etc. for the treatment of inflammation or pruritis. The enzyme inhibition is demonstrated by adding the potato juice directly to a mixture of the enzyme.

U.S. Pat. No. 6,331,295 B1 discloses the use of a solid composition for prevention of skin irritation such as diaper rash comprising an organophilic clay dispersed in a water-permeable superabsorbent polymer matrix. The organophilic clay is selected from a group consisting of natural and synthetic montmorillonite, bentonite, etc.

U.S. Pat. No. 6,207,596 B1 discloses a disposable pre-moistened wipe containing an antimicrobial protease inhibitor such as an aromatic diamidine.

US Patent application US 2003/0206944 A1 discloses a wound dressing composed of a cotton cellulose matrix with an active agent that is an inhibitor or sequestrant of a neutrophil-derived cationic protease, such as elastase. The active agent could be inhibitors selected from a group consisting of di- and tri-peptides, or sequestrants selected from a group consisting of sulphonyl, phosphate, or aldehyde groups associated with the matrix.

US Patent application US 2004/0028708 A1 discloses the use of a skin protectant cream with an enzyme blocking compound. The enzyme blocking compound is selected from zinc sulfate, zinc chloride, zinc oxide, zinc lactate, or combinations thereof.

US Patent application US 2003/0104019A1 discloses a solid topical composition comprising a swellable clay and a peptizing agent for the treatment or reduction of enzymatic dermatitis, such as perineal dermatitis, caused by urine. The swellable clay is selected from a group consisting of pyrophillite, talc, smectite, sepiolite, zeolite, palygorskite, and mixtures thereof. The peptizing agent is selected from a group consisting of tetrasodium or potassium pyrophosphate, sodium hexametaphosphate, sodium citrate, sodium polyacrylate, etc.

These references do not suggest or disclose delivering enzyme inhibition compositions using an adhesive matrix.

BRIEF DESCRIPTION OF THE DRAWINGS

FIG. 1 is a graph charting the percentage of inhibition at time intervals using Chymotrypsin inhibition.

FIG. 2 is a graph charting the percentage of inhibition at time intervals using Trypsin inhibition.

FIG. 3 is a graph charting the percentage of inhibition at time intervals using Elastase inhibition.

FIG. 4 is a graph charting the percentage of inhibition at time intervals using Pepsin inhibition.

DESCRIPTION OF INVENTION

The present invention relates to incorporating one or more enzyme de-activating agents based on tubers into adhesives such as hydrocolloid adhesives for wafer barrier application to the skin in ostomy and wound care. The adhesive may, for example, be included in a wafer, thin sheet or film. In addition, this invention may be used as a coupling adhesive in devices that come in contact with feces and wound exudates.

Accordingly, the adhesive composition of the present invention includes an adhesive component and an enzyme inhibiting component. The enzyme inhibiting component may be one or more inhibitors derived from tubers, such as from potatoes. The adhesive component may be a hydrocolloid adhesive that includes a rubber matrix and one or more fillers. The rubber matrix is selected from the group consisting of polyisobutylene, polybutadiene, polyisoprene, styrenic block copolymers, amorphous polyolefins, polyurethanes, acrylics, silicones, polyvinyl pyrollidone (PVP), ethylene vinylacetate (EVA), polyvinyl methylether, and combinations thereof. The fillers are hydrocolloids selected from the group consisting of carboxymethyl cellulose, sodium carboxymethyl cellulose, carboxyethylmethyl cellulose, carboxypropyl cellulose, carboxyethyl cellulose, pectin, gelatin, agar, alginate, carageenan, cellulose, guar gum, karaya gum, locust bean gum, xanthan gum, chitosan and its derivatives, starch, pullulan, beta-glucan, gellan, curdlan, and combinations thereof.

It is alternatively possible for the adhesive component to be selected from the group consisting of hydrocolloid adhesives, polyisobutylene, polybutadiene, polyisoprene, styrenic block copolymers, amorphous polyolefins, polyurethanes, acrylics, silicones, polyvinyl pyrollidone (PVP), ethylene vinylacetate (EVA), polyvinyl methylether, and combinations thereof.

EXAMPLES

Table 1 shows the composition of the adhesives used for evaluation. Adhesive A is control hydrocolloid adhesive.

Adhesive B is does not contain gelatin or potato protein. Adhesive C is similar to Adhesive A where the gelatin is replaced with potato protein.

Adhesive Mixing

The adhesives were mixed in a Haake mixer at 230 F. The polyisobutylene rubber was initially mixed followed by rest of the ingredients, once the rubber melted. Those skilled in the art will recognize that many methods of blending the ingredients are suitable for preparing these adhesives and that the process described above in no way limits the scope of the invention disclosed herein. The resulting adhesives were heat pressed between two silicone releases papers to form a sheet of about 3.5 mm thickness.

Determination of Enzyme Inhibition

Each adhesive was cut into pieces of about 7.5 mm×7.5 mm×2.0 mm. The adhesive pieces were placed in separate vials. For each adhesive composition, four different enzymes, Chymotrypsin, Trypsin, Elastase, and Pepsin were tested separately. In addition, the pure protein powder was evaluated at two concentrations, 1% w/v and 4% w/v. The vials were incubated at 37 C and the enzyme activity was monitored using absorption-emission spectroscopy. Tables 2 and 3 list the enzymes and their concentration used for the study, and the experimental matrix, respectively. Pepsin is released in the stomach and the other three enzymes are released by the pancreas. All of these enzymes are present in feces. Elastase is also present in wounds.

TABLE 1

Adhesive compositions for enzyme activity study

| Ingredient | Adhesive A | Adhesive B | Adhesive C |
|---|---|---|---|
| Polyisobutylene | 40 | 40 | 40 |
| Sodium carboxymethyl cellulose | 20 | 30 | 20 |
| Pectin | 20 | 30 | 20 |
| Gelatin | 20 | — | — |
| Protagold Potato protein | — | — | 20 |

TABLE 2

Concentration of enzymes used in enzyme activity study

| Vial # | Ingredient | Enzyme concentration, nM | pH | Buffer |
|---|---|---|---|---|
| 1 | Chymotrypsin | 0.2 nM | 7.5 | HEPES |
| 2 | Trypsin | 0.06 nM | 7.5 | HEPES |
| 3 | Elastase | 0.17 µg/ml | 8.0 | Tris-HCl |
| 4 | Pepsin | 0.05 µg/ml | 2.1 | Citrate |

TABLE 3

Experimental matrix for enzyme activity study

| | Chymotrypsin | Trypsin | Elastase | Pepsin |
|---|---|---|---|---|
| Potato protein 1% w/v | X | X | X | X |
| Potato protein 4% w/v | X | X | X | X |
| Adhesive A | X | X | X | X |
| Adhesive B | X | X | X | X |
| Adhesive C | X | X | X | X |

Results

Table 4 shows the effect of adding potato protein to a pressure sensitive adhesive. It can be seen that the peel strength to stainless steel and tack for Adhesive C with 20% protein is comparable to the control Adhesive A. In addition, Table 4 shows that the tack values of conventional pressure sensitive adhesives with and without 20% w/w protein are comparable.

TABLE 4

Effect of Protagold potato protein on peel and tack properties of pressure sensitive adhesives

| Adhesives | Stainless steel Peel Strength, N/in (ASTM D3330)) | Tack, g (TA Texture Analyzer) |
|---|---|---|
| Hydrocolloid adhesives | | |
| Adhesive A (Control) | 7.6 +/− 0.15 | *630 +/− 106 |
| Adhesive C (20% Protagold) | 8.9 +/− 0.2 | *716 +/− 127 |
| Non-hydrocolloid adhesives | | |
| Morstik 125 (100%) | N/A | **464 +/− 32 |
| Morstik 125 (80%) + (20% Protagold) | N/A | **169 +/− 26 |
| Gelva 788 (100%) | N/A | **445 +/− 64 |
| Gelva 788 (80%) + (20% Protagold) | N/A | **467 +/− 29 |
| Bio-PSA 7-4601 (100%) | N/A | **748 +/− 110 |
| Bio-PSA 7-4601 (80%) + (20% Protagold) | N/A | **607 +/− 51 |

*Test force - 450 g;
**Test force - 100 g;
N/A Not Available
Protagold - Potato protein from AVEBE America Inc.
Morstik 125 - Rubber adhesive from Rohm & Haas
Gelva 788 - Acrylic adhesive from Solutia, Inc.
Bio-PSA 7-4601 - Silicone adhesive from Dow Corning Corporation FIGS. 1-4 show that the pure protein powder has good inhibiting capability for all four enzymes at both concentrations, 1% w/v and 4% w/v. Surprisingly, it was observed that the Adhesive C, the adhesive composition with the potato protein inhibitor, shows inhibiting capabilities to all four enzymes. It was determined by feel that Adhesive C maintains suitable tackiness to function as an adhesive.

The invention claimed is:

1. An adhesive composition for use in an ostomy appliance to provide adhesion and inhibit fecal enzymes, said composition comprising:
   a pressure-sensitive, gelatin-free hydrocolloid adhesive component; and
   an enzyme inhibiting protein component derived from potatoes, wherein the combined components provide adhesion and inhibit the fecal enzymes chymotrypsin, trypsin, elastase and pepsin, said inhibition increasing over at least 4 hours at 37° C.

2. The adhesive composition of claim 1, wherein said adhesive component is a rubber-based polyisobutylene.

3. The adhesive component of claim 2 comprising 40% polyisobutylene, 20% carbomethylcellulose, 20% pectin and 20% protagold potato protein.

4. The adhesive composition of claim 1, wherein said enzyme inhibiting component is Protagold potato protein.

* * * * *